United States Patent
Cheng et al.

(10) Patent No.: US 6,942,769 B2
(45) Date of Patent: Sep. 13, 2005

(54) ELECTROCHEMICAL SENSOR STRIP WITH LOW POROSITY SCREEN

(75) Inventors: Chen-Heng Cheng, Taichung (TW); Jung Cheng, Taichung (TW); Jung-Tzu Chang, Taichung (TW)

(73) Assignee: BT Medical Corp., Ft. Lauderdale, FL (US)

( * ) Notice: Subject to any disclaimer, the term of this patent is extended or adjusted under 35 U.S.C. 154(b) by 157 days.

(21) Appl. No.: 10/634,560

(22) Filed: Aug. 5, 2003

(65) Prior Publication Data

US 2005/0029097 A1 Feb. 10, 2005

(51) Int. Cl.[7] .................... G01N 27/403; G01N 27/327; G01N 27/333
(52) U.S. Cl. .................. 204/400; 204/403.02; 204/416
(58) Field of Search ............... 204/400, 403.01–403.15, 204/416–418

(56) References Cited

U.S. PATENT DOCUMENTS

| | | | |
|---|---|---|---|
| 4,897,173 A | 1/1990 | Nankai et al. | 204/403 |
| 5,120,420 A | 6/1992 | Nankai et al. | 204/403 |
| 5,141,868 A | 8/1992 | Shanks et al. | 435/288 |
| 5,628,890 A | 5/1997 | Carter et al. | 204/403 |
| 6,129,823 A | 10/2000 | Hughes et al. | 204/409 |
| 6,627,057 B1 * | 9/2003 | Bhullar et al. | 204/403.01 |

FOREIGN PATENT DOCUMENTS

WO WO92/17778 10/1992

* cited by examiner

*Primary Examiner*—Alex Noguerola
(74) *Attorney, Agent, or Firm*—Robert C.. Kain, Jr.; Fleit Kain

(57) ABSTRACT

The electrode test strip is used with an electrochemical sensor for measuring an analyte in an aqueous sample, e.g., glucose in blood. The electrode strip includes an elongated electrode support, a first and second electrode on the support, a slotted dielectric layer, a screen and a slotted cover layer, all disposed atop each and atop the electrodes in the support. The dielectric layer and the cover layer are typically adhesively attached (the adhesive layers further define the slot). The slot is open to the terminal end of the test strip and the cover. The screen, interposed in the slot, has a porosity between 10%–40% to control analyte flow and volume in the slot and over the test area defined by electrode legs. Further refinements include utilizing a surfactant on the screen.

10 Claims, 1 Drawing Sheet

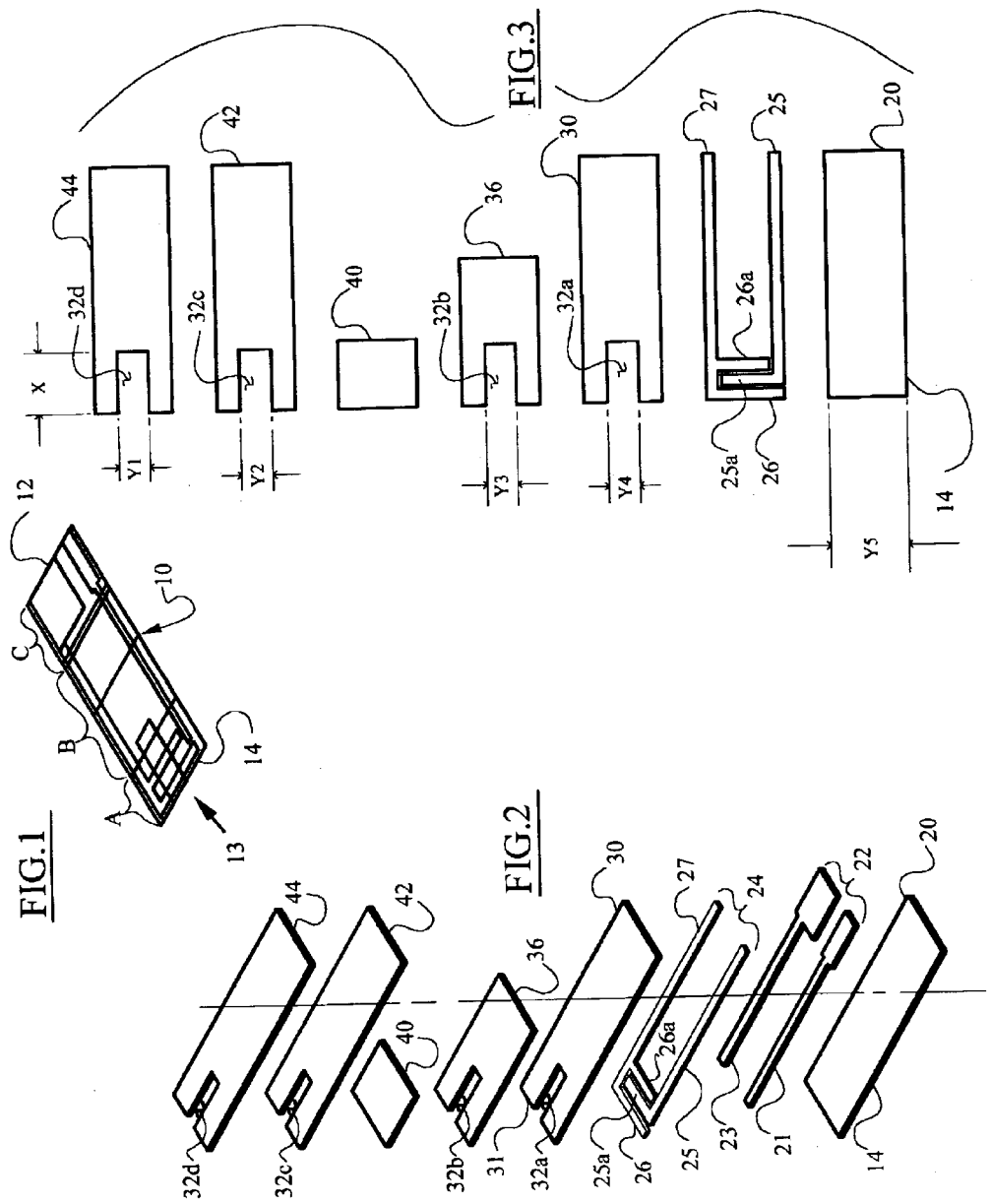

ELECTROCHEMICAL SENSOR STRIP WITH LOW POROSITY SCREEN

The present invention relates to an electrode strip for use in an electrochemical sensor for measuring an analyte in an aqueous sample, and particularly a sensor test strip having a low porosity screen to control analyte flow and volume over the electrode test area.

BACKGROUND OF THE INVENTION

An electrode test strip is typically utilized in conjunction with an apparatus that senses a change in the electrical system based upon an electrochemical reaction on the electrode strip which is indicative of the presence, absence or amount of a certain chemical or chemical composition (an analyte) in an aqueous sample deposited on the electrode test strip. For example, without limiting the utilization of the present invention, electrode strips are used in association with electrochemical sensors which detect the amount of glucose in a patient's blood. Diabetic patients use disposable electrode strips which are loaded into the sensory apparatus multiple times during the day to detect their glucose level.

Some examples of electrochemical sensors and electrode strips are:

U.S. Pat. No. 4,897,173 entitled Biosensor and Method for Making the Same.

U.S. Pat. No. 5,120,420 entitled Biosensor and a Process for Preparation Thereof.

U.S. Pat. No. 5,141,868 entitled Device for Use in Chemical Test Procedures.

U.S. Pat. No. 5,628,890 Electrochemical Sensor.

U.S. Pat. No. 6,129,823 Low Volume Electrochemical Sensor.

International Publication No. WO92/17778 entitled Analytical Devices.

OBJECTS OF THE INVENTION

It is an object of the present invention to provide an electrode strip for use in an electrochemical sensor for measuring an analyte in an aqueous sample.

It is another object of the present invention to provide an electrode strip which has a low porosity screen to control analyte flow and volume in the testing area over the electrode configuration.

It is another object of the present invention to provide an open top slot extending from the top cover through to the electrode working area, excepting the low porosity screen, and the slot being formed in several layers and in adhesive or glue between the various test strip layers.

It is another object of the present invention to utilize the slot and the low porosity screen to keep the volume and flow of blood sample (or an aqueous solution) needed for testing about the test area at relatively low levels or at a controlled level.

It is a further object of the present invention to provide an electrode strip which provides a tactile response to the user and which enables the user to direct the aqueous sample into the electrode-defined testing area on the electrode strip.

SUMMARY OF THE INVENTION

The electrode strip is utilized in connection with an electrochemical sensor for measuring an analyte in an aqueous sample, such as, without limitation, measuring the amount of glucose in a patient's blood. The electrode strip includes an elongated electrode support, a first and second electrode on the support for electrochemical analysis of the analyte, a dielectric layer, a screen and a cover layer, all disposed atop each other and atop the electrodes on the support. The dielectric layer and the cover layer, typically adhesively attached, define an open top slot (the slot also defined by the adhesive layers) wherein the slot is open to the terminal end of the elongated electrode support and open on the cover. The slot extends over at least forwardly and rearwardly disposed electrode legs thereby forming a vent over those electrode legs. The screen, interposed as a layer in the test strip and necessarily disposed in the slot, has a porosity between 10%–40% to control analyte flow and volume in the slot and mainly over the test area defined by electrode legs. Further refinements to the invention include utilizing a surfactant on the screen to enhance wetting by the analyte. The slot creates a terminal end hook which provides a tactile response to the user enabling more efficient gathering of the aqueous solution in the slot and hence over the test area defined by electrode legs.

BRIEF DESCRIPTION OF THE DRAWINGS

Further objects and advantages of the present invention can be found in the detailed description of the preferred embodiment, when taken in conjunction with the accompanying drawings in which:

FIG. 1 diagrammatically illustrates the assembled electrode strip.

FIG. 2 diagrammatically illustrates an exploded perspective view of the electrode strip showing the various layers of the strip in FIG. 1.

FIG. 3 diagrammatically illustrates a plan view of most of the strip layers excluding the initial electrode layer illustrated in FIG. 2.

DETAILED DESCRIPTION OF THE PREFERRED EMBODIMENT

The present invention relates to an electrode strip 10 for use in an electrochemical sensor (not shown) for measuring an analyte in an aqueous sample. Electrode strip 10 is generally a disposable item which is inserted at rear terminal end 12 into an electrochemical sensor which is not shown in the figures. The strip may be permanently mounted in the sensor in some situations. The aqueous sample containing the analyte is deposited as shown by arrow 13 at forward terminal end 14 of strip 10. The electrode strip is generally configured as having a forward end section A, a central section B and a rearward end section C. Rearward end section C is electrically connected to the electrochemical sensor. One embodiment of electrode strip 10 is approximately 3 cm long and approximately 5 mm wide. A large number of test strips are made on a sheet or platform and the sheet is cut to form individual test strips.

FIG. 2 diagrammatically illustrates a perspective, exploded view of the layers forming electrode strip 10 and FIG. 3 shows a plan view of the view of those layers excepting the initial electrode layer clearly shown in FIG. 2. FIGS. 2 and 3 are discussed concurrently herein and similar numerals designate similar items in the figures. Electrode strip 10 has an elongated electrode support or base 20, preferably made of polyester (PET). Other material for the base may be utilized. Base support 20 has a terminal end 14 and a width Y5.

An electrode system consisting of initial electrode elements 22 and supplemental electrode elements 24 are disposed on top of support base 20. Preferably, initial electrode system 22 consists of silver ink which is printed onto electrode support base 20. Electrodes 21, 23 are generally electrically isolated from each other. Supplemental electrode system 24 is also printed onto electrode support base 20 and is typically carbon ink. Supplemental electrode system 24 includes electrically separated electrodes 25, 27. Herein, systems 22, 24 (consisting of separate electrodes 21, 23, 25 and 27) are referred to collectively as the "electrode system." One of these electrodes in FIG. 2, electrode 27, has a forwardly disposed electrode leg 26. Electrode 25 has a rearwardly disposed electrode leg 25a. Electrodes 27 and 25 are sometimes called first and second electrodes. Legs 26, 25a are generally electrically separated and are disposed relatively near terminal end 14 of electrode support base 20 in region A (FIG. 1). In general, the area above and about electrode legs 26, 25a and supplemental leg 26a form the test area for the analyte which is drawn into terminal end 14 as shown by arrow 13 in FIG. 1. Essentially, the aqueous solution with the subject analyte is drawn in by the wicking action of the porous screen.

Dielectric layer 30 is disposed atop electrode system 22, 24. Dielectric 30 has or defines a slot 32a near its terminal edge 31. Terminal edge 31 is disposed at a co-extensive position with respect to terminal edge 14 of electrode support base 20. Dielectric 3 is a UV dielectric. Generally, all layers have a co-extensive terminal edge or end, that is, co-extensive with terminal end 31.

The next layer is an adhesive layer 36 disposed atop dielectric layer 30. Adhesive layer 36 also includes a slot 32b at its forward end section. A low porosity screen 40 is disposed at the terminal end section A (FIG. 1) of adhesive layer 36.

A second adhesive layer 42 is disposed atop low porosity screen 40. Adhesive layer 42 includes a slot 32c at its forward end section. A top cover layer 44, typically made of polyester, covers electrode strip 10. Top cover layer 44 includes a forward end slot 32d.

When assembled as shown in FIG. 1, the open-topped slot formed by slot layers 32a, 32b, 32c and 32d form an open vent slot in electrode strip 10 which provides several advantages. First, the open-topped slot establishes a vent for the test area which is generally in the region of electrode legs 26, 25a and 26a at the forward end section A of the test strip. See section A in FIG. 1. Further, the open-topped slot establishes a tactile response for the patient which enables the patient to more accurately deposit and distribute the aqueous sample into the test area adjacent and atop electrode legs 26, 25a, 26a. Further, the open top slot forms a hook which enhances the gathering of the aqueous sample in the test area.

In addition, low porosity screen 40, which somewhat partially blocks the slot 32a, 32b, 32c and 32d, controls analyte flow and volume in areas not directly over the electrode test area defined at electrode legs 26, 25a, 26a. Further, the low porosity screen 40 establishes somewhat of a testing chamber with the open-topped slot. The low porosity screen keeps a volume of analyte or blood sample needed for testing at a moderately low level. The screen wicks samples into the test area at an near electrode legs 26, 25a, 26a.

The low porosity screen 40 preferably has a porosity of between 10% and 40% to control analyte flow and volume. The screen preferably has a mesh opening of about 15–20 microns. The screen maybe made of polyester, nylon or polypropylene. Preferably, a polyester monofilament is utilized with a 3:3 twill weave, a mesh opening of 17 microns, a mesh count of 555 square inches and an open area of 32%. The thread diameter is 40 microns. In addition, the screen may be traded with a surfactant to aid in wetting. One surfactant, manufactured by Sigma is called diocyl sulfosuccinate (DOSS). In addition 0.2% to about 2% of other surfactants may be utilized such as, for example, Surfynol a surfactant manufactured by Air Products, Triton x-100 manufactured by Pierce Biotechnology, and Brij manufactured by JT Baker. Another low porosity mesh is obtained from Saaticare under the tradename Saatifyl polyester PES 18/13. The Saaticare screen has a mesh opening of 18, an open area of 13%, a mesh count of 500 square inches, a thread diameter of 31 microns and is typically treated with surfactants.

Layers of adhesive or glue 36,42, are the intermediate adhesive layers between slotted dielectric 30 and screen 40 (with respect to slotted intermediate adhesive layer 36) and slotted cover 44 and screen 40 (with respect to slotted intermediate adhesive layer 42). The adhesive layers define slot segments as shown herein.

The width of the slot is limited in that slot widths shown generally as "Y" in FIG. 3 are limited to between 0.4 mm and 1.8 mm. Slots larger or smaller than those dimensions do not seem to create an acceptable testing chamber generally above and about electrode legs 26, 25a, 26a. In one embodiment, the slots 32a, 32b, 32c and 32d have the following dimensions. Dimension Y1 for slot 32d is 1.8 mm, Y2 is 2 mm, Y3 is 2.1 mm and Y4 is 1.7 mm with the test strip width Y5 approximately 6.2 mm. The elongated length of the slot in one working embodiment is 5.6 mm. Slot length X slightly exceeds the working area above electrode legs 26, 25a, 26a. The screen 40 runs at least the entire length of the slot.

Other surfactants may be utilized to enhance fluid control and analyte volume in the testing area. Examples of potential other surfactants are:

Dioctyl Suldosuccinate synonyms include: oxol, doxinate, colace, molatoc, norval, obston, rapisol, dioctyl sodium succinate, docusate sodium, cloace, bis(2-ethylhexyl) sulfosuccinate sodium salt, aerosol OT, bis(2-ethylhexyl) sodium sulfosuccinate, dioctyl sulfosuccinate sodium salt. Triton X-100 synonyms are: polyethylene glycol P-1,1,3,3-tetramethylbutylphenyl ether, octyl phenol ethoxylate, 4-octylphenol polyethoxylate, Mono 30.

In addition, the electrode system 22, 24 may be treated with certain enzymes, and are typically treated with certain enzymes unique to an analyte to be tested in aqueous solution. Enzymes within the following table are currently utilized:

|  |  |  | 25 ml | 25 ml |
|---|---|---|---|---|
| $KH_2PO_4$ | 300 mM | 35.25 g/L | 0.88125 g | |
| $K_2HPO_4 \cdot H_2O$ | | 9.3562 g/L | 0.2339 | |
| Natrosol | 1.50% | | 0.375 | |
| PVP40 | 0.50% | | 0.125 | |
| Triton | 0.05% | | 0.0125 ml | |
| Potassium Ferricyanide | 300 mM | | 2.469 g | |
| Glucose Oxidas | 3850 KU/L | | 96.25 KU = 337.8 mg Bio | |
| pH +6.0 | | | | |

The claims appended hereto are meant to cover modifications and changes within the scope and spirit of the present invention.

What is claimed is:

1. An electrode strip for use in an electrochemical sensor for measuring an analyte in an aqueous sample, comprising:

an elongated electrode support having a terminal end;

a first and a second electrode on said support for electrochemical analysis of said analyte, said first electrode having a forwardly disposed leg which is near said terminal end and second electrode having a rearwardly disposed leg which is rearwardly disposed with respect to both said terminal end and said forward leg of said first electrode;

a dielectric layer, a screen, and a cover layer, all disposed atop each other and atop said electrodes and said support;

said dielectric layer and cover layer having an open-topped slot therein, said slot being open to said terminal end and extending over at least said forwardly and rearwardly disposed electrode legs, said slot forming a vent at least over said forwardly and rearwardly disposed electrode legs; and said screen having a porosity between 10% and 40% to control analyte flow and volume in said slot and over said forwardly and rearwardly disposed electrode legs.

2. An electrode strip as claimed in claim 1 including intermediate layers of adhesive, one adhesive layer disposed between said screen and said dielectric and another adhesive layer disposed between said screen and said cover layer, each intermediate adhesive layer having a respective slot generally coextensive with said slot in said dielectric layer and said cover layer.

3. An electrode strip as claimed in claim 1 wherein said screen carries a surfactant to enhance wetting by said analyte.

4. An electrode strip as claimed in claim 3 wherein the surfactant is one selected from the group consisting of sulphonal and sulfosuccinate.

5. An electrode strip as claimed in claim 1 where said screen is a polyester mesh screen with a mesh opening of about 15–20 microns.

6. An electrode strip as claimed in claim 1 wherein the screen is made from a material selected from the group consisting of polyester, nylon and polyproplene.

7. An electrode strip as claimed in claim 6 wherein said screen carries a surfactant to enhance wetting by said analyte and wherein the surfactant is one selected from the group consisting of sulphonal and sulfosuccinate.

8. An electrode strip as claimed in claim 1 wherein the screen has a mesh opening of about 15–20 microns and a mesh size of about 500 per square inch.

9. An electrode strip as claimed in claim 1 wherein the terminal end of said support and said slot gathers said analyte.

10. An electrode strip as claimed in claim 1 wherein said support includes a forward end section ending at said terminal end and a central section and a rearward end section; said screen is disposed generally over said forwardly and rearwardly disposed electrodes and said forward end section of said support and is not disposed over said central section and rearward end sections of said support.

* * * * *